Figure 1A:
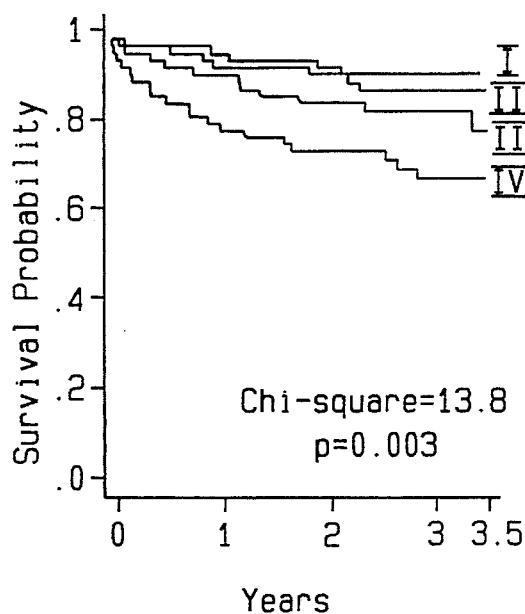
Figure 1B:
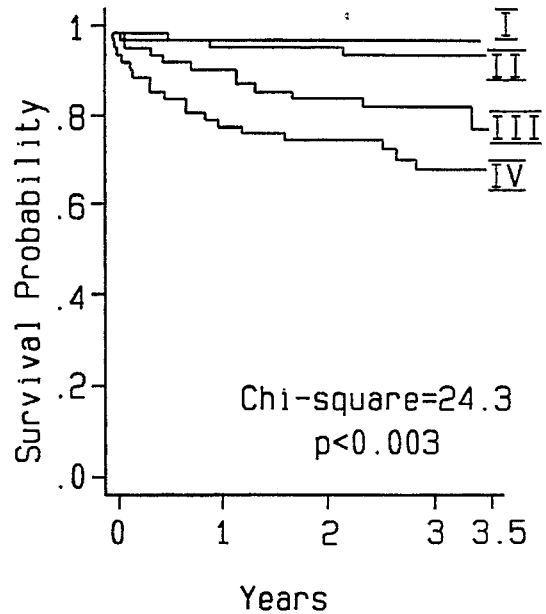
Figure 1C:
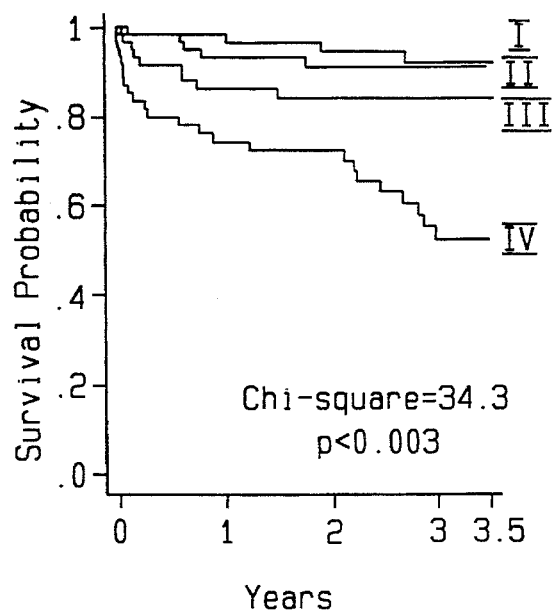
Figure 1D:
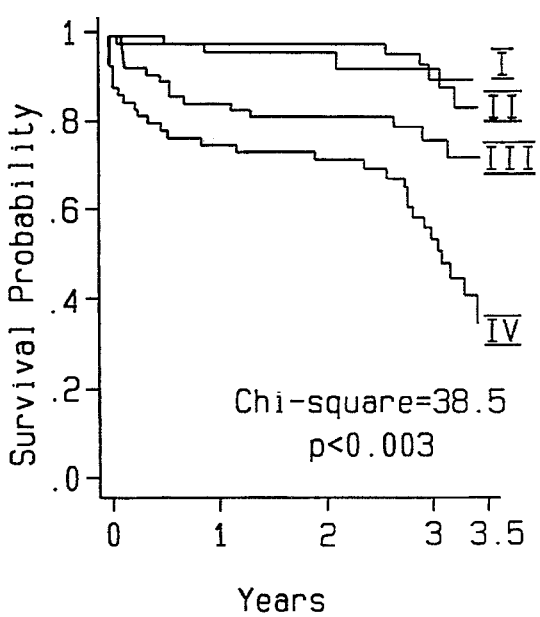

United States Patent [19]

Hall

[11] Patent Number: 5,498,524
[45] Date of Patent: Mar. 12, 1996

[54] METHOD OF TESTING FOR HEART FAILURE RISK

[75] Inventor: Christian Hall, Snarøya, Norway

[73] Assignee: Medinnova S.F., Oslo, Norway

[21] Appl. No.: 186,680

[22] Filed: Jan. 25, 1994

[30] Foreign Application Priority Data

Mar. 12, 1993 [GB] United Kingdom .................... 9305142

[51] Int. Cl.$^6$ ..................................................... G01N 33/68
[52] U.S. Cl. ............................ 435/7.1; 435/7.9; 435/7.92; 435/7.93; 435/7.95; 436/501; 436/518; 436/536; 436/539; 436/542; 436/811; 530/350; 530/388.24; 530/389.2
[58] Field of Search ..................................... 436/518, 542, 436/501, 811, 536, 539; 435/7.1, 7.9, 7.92, 7.93, 7.95, 975; 530/350, 388.24, 389.2

[56] References Cited

PUBLICATIONS

Buckley, M. G. et al. N. terminal pro Atrial Natriuretic Peptide in Human Plasma. American Journal of Hypertension 3:933–935, 1990.

Gottlieb S. S. et al. Prognostic Importance of Atrial Natriuretic Peptide in Patients with Chronic Heart Failure. Journal of the American College of Cardiology 13(7): 1534–1539, 1989.

Hall, C. et al. N. terminal Proatrial Natriuretic Factor. An Independent predictor of longterm prognosis after myocardial infarction. Circulation 89(5): 1934–42, 1994.

Dellerich, M. Enzyme Immunoassay: A Review. Journal of Clinical Chemistry and Clinical Biochemistry 22(12) 895–904, 1984.

Svanegaard J. Plasma Concentration of atrial natriuretic peptide at admission and risk of cardiac death in patients with acute myocardial infarction. British Heart Journal 68:38–42, 1992.

Thomas, C. L., ed. Taber's Cyclopedic Medical Dictionary, 1985. Philadelphia: F. A. Davis. pp. 729–730.

D. L. Vesely et al., The N–Terminus Of The Atrial Natriuretic Factor Prohormone In The Pleural Fluid Of Congestive Heart Failure Patients, Chest, 97, pp. 1295–1298 (1990).

R. P. Wyeth et al. The N–Terminus, C–Terminus, And Vessel Dilator Of The ANF Prohormone Are Present In The Urine And Increase With Ventricular Fibrillation, Biochem. and Biophys Rsch. Com, 173, pp. 1030–1037 (1990).

DeBold A. J., Borenstein H. B., Veress A. T., Sonnenberg H. A rapid and potent natriuretic response to intravenous injection of atrial myocardial extract in rats. Life Sci 1981; 28: 89–94.

Flynn T. G., DeBold M. L., DeBold A. J., The aminoacid sequence of an atrial peptide with potent diuretic and natriuretic properties. Biochem Biophys Res Commun 1983; 117: 859–65.

Miyata A., Kangawa K., Toshimori T., Hatch T., Matsuo H. Molecular forms of atrial natriuretic polypeptides in mammalian tissues and plasma. Biochem Biophys Res Commun 1985; 129: 248–55.

Thibault G., Garcia R., Gutkowska J., Bilodeau J., Lazure C., Seidah N. G., Chretien M., Genest J., Cantin M. The propeptide Asn 1–Tyr 126 is the storage form of rat atrial atrial natriuretic factor. Biochem J 1987; 241: 265–72.

Sundsfjord J. A., Thibault G., Larochelle P., Cantin M. Identification and plasma concentrations of the N–terminal fragment of proatrial natriuretic factor in man. J Clin Endocrinol Metab 1988; 66: 605–10.

Thibault G., Murthy K. K., Gutkowska J., Seidah N. G., Lazure C., Chretien M. & Cantin M. NH2– terminal fragment of rat pro–atrial natriuretic factor in the circulation: identification, radioimmunoassay and half–life. Peptides 1988; 9: 47–53.

Itoh H., Nakao K., Sugawara A., Saito Y., Mukoyama M., Morii N., Yamada T., Shiono S., Arai H., Hosoda K., Imura H. Gamma–Atrial natriuretic polypeptide (gammaANP) –derived peptides in human plasma: cosecretion of N–terminal gammaANP fragment and alfaANP. J Clin Endocrinol Metab 1988; 67: 429–37.

Yandle T. G., Richards A. M., Nicholls M. G. Cueno R., Espiner E. A., Livesey J. H. Metabolic clearance rate and plasma half life of alfa–human atrial natriuretic peptide in man. Life Sci 1986; 38: 1827–33.

Maack T. Receptors of atrial natriuretic factor. Annu Rev Physiol 1992; 54: 11–27.

Stephenson S. L. Kenny A. The hydrolysis of alpha–human atrial natriuretic peptide by pig kidney microvillar membranes is initiated by endopeptidase 24.11. Biochem J 1987; 243: 183–87.

Winters C. J., Sallman A. L., Baker B. J., Meadows J., Rico D. M., Vesely D. L. The N–terminus and a 4,000–MW peptide from the midportion of the N– terminus of the atrial natriuretic factor prohormone each circulate in humans and increase in congestive heart failure. Circulation 1989; 80: 438–49.

Burnett et al 1986 Science 231: 1145.

Nelesen R. A., Dimsdale J. E., Ziegler M. G. Plasma atrial natriuretic peptide is unstable under most storage conditions. Circulation 1992; 86: 463.

Dietz J. R. Release of natriuretic factor from rat heart–lung preparation by atrial distension. Am J Physiol 1984; 247:R1093–6.

Dietz J. R., Nazian S. J., Vesely D. L. Release of ANF. proANF 1–98, and proANF 31–67 from isolated rat atria by atrial distension. Am J Physiol 1991; 260: H1774–8.

Richards A. M., Cleland J. G. F., Tonolo G., McIntyre G. D., Leckie B. J., Dargie H. J., Ball S. G., Robertson J. I. S. Plasma alpha natriuretic peptide in cardiac impairment. BMJ 1986; 293: 409–12.

(List continued on next page.)

Primary Examiner—Michael P. Woodward
Assistant Examiner—Jeffrey Stucker
Attorney, Agent, or Firm—Pennie & Edmonds

[57] ABSTRACT

The peptide N-terminal pro-ANF, which is present in body fluids such as plasma, has been found to be an effective predictor of heart failure and the invention provides prediction and screening methods based upon in vitro assaying of N-terminal pro-ANF in body fluids.

11 Claims, 2 Drawing Sheets

PUBLICATIONS

Mathisen P., Hall C., Simonsen S. Comparative study of atrial peptides ANF(1–98) and ANF(99–126) as diagnostic markers of atrial distension in patients with cardiac disease. Scand J Clin Lab Invest 1993; 53: 41–9.

Gottlieb S. S., Kukin M. L. Ahern D., Packer M. Prognostic importance of atrial natriuretic peptide in patients chronic heart failure. J Am Coll Cardiol 1989; 13: 1534–9.

Swedberg K., Eneroth P., Kjekshus J., Wilhelmsen L. Hormones regulating cardiovascular function in patients with severe congestive heart failure and their relation to mortality. Circulation 1990; 82: 1730–6.

Svanegaard J., Angelo–Nielsen K., Pindborg T. Plasma concentration of atrial natriuretic peptide at admission and risk of cardiac death in patients with acute myocardial infarction. Br Heart J 1992; 68: 38–42.

Davis K. M., Fish L. C. Elahi D., Clark B. A., Minaker K. L. Atrial natriuretic peptide levels in the prediction of congestive heart failure risk in the frail elderly. JAMA 1992; 267: 2625–9.

Pfeffer M. A., Braunwald E., Moye L. A., al e. Effect of captopril on mortality and morbidity in patients with left ventricular dysfunction after myocardial infarction. N Engl J Med 1992; 327: 669–77.

Moye L. A. Pfeffer M. A., Braunwald E. Rationale, design and baseline characteristics of the survival and ventricular enlargement trial. Am J Cardiol 1991; 68: 70–9D.

Rouleau J. L., Moye L. A., de Champlain J., Klein M., Bichet D., Packer M., Dagenais G., Sussex B., Arnold M., Sestier F., Parker J., McEwan M., Bernstein V., Cuddy T., Delage F., Nadeau C., Lamas G., Gottlieb S., McCans J. Pfeffer M. Activation of Neurohumoral Systems Following Acute Myocardial Infarction. Am J. Cardiol 1991; 68: 80–6D.

Mettauer B., Rouleau J. L., Bichet D., Kortas C., Manzini C., Tremblay G., Chatterjee K. Differential long–term intrarenal and neurohormonal effects of captopril and prazosin in patients with chronic congestive heart failure: importance of initial plasma renin activity. Circulation 1986; 73: 492–502.

Cohn J. N., Levine T. B., Olivari M. T., Garberg V., Lura D., Francis G., Simon A., Rector T. Plasma norepinephrine as a guide to prognosis in patients with chronic congestive heart failure. N Engl J Med 1984; 311:819–23.

Edwards B. S., Zimmerman R. S., Schwab T. R., Heublein D. M., Burnett J. C.: Atrial stretch, not pressure, is the principal determinant controlling the acute release of atrial natriuretic factor. Circ Res 1988; 62: 191–5.

Hintze T. H., McIntyre J. J., Patel M. B., Shapiro J. T., DeLeonardis M., Zeballos G. A., Loud A. V. Atrial wall function and plasma atriopeptin during volume expansion in conscious dogs. Am J Physiol 1989; 256: H713–H719.

Grossman W., Jones D., McLaurin L. P., Wall stress and patterns of hypertrophy in the human left ventricle. J Clin Invest 1975: 56; 56–64.

White H. D., Norris R. M., Brown M. A., Brandt P. W. T., Whitlock R. M. L., Wild C. J. Left ventricular end–systolic volume as the major determinant of survival after recovery from myocardial infarction. Circulation 1987; 76(1): 44.

Cohn J. N., Johnson G., Ziesche S., Cobb F., Francis G., Tristani F., Smith R., Dunkman W., Loeb H., Wong M., Bhat G., Goldman S., Fletcher R., Doherty J., Hughes C., Carson P., Cintron G., Shabetai R., Haakenson C. A comparison of enalapril with hydralazine–isosorbide dinitrate in the treatment of chronic congestive heart failure. N Engl J Med 1991; 325: 303–10.

METHOD OF TESTING FOR HEART FAILURE RISK

The present invention relates to a method for predicting the development of heart failure in susceptible patients.

Heart failure is a common clinical syndrome, especially among elderly people. Population surveys indicate that the condition affects about 2% of the total population in the western world. The syndrome usually presents itself with an insidious onset with unspecific symptoms such as breathing difficulties (dyspnea) on exertion, fatigue and peripheral oedemas. Once heart failure occurs, a vicious circle sets in where as a result of the heart not working well enough to support the body the heart failure gets worse. The end result is generally gradual deterioration of the patient, and development of severe heart failure often leading to cardiovascular mortality.

Heart disease represents a significant drain on health resources in many major countries, and whilst an early diagnosis may help in controlling the condition and preventing rapid regression to severe heart failure, it would obviously be preferable to be able to identify those patients in which heart failure is likely to occur before it actually does so, i.e. to prognose rather than diagnose.

Unfortunately, there are at present no completely satisfactory methods for predicting the likelihood of heart failure. Problems frequently observed with such methods are insufficient accuracy and sensitivity, and the disadvantages of the necessity for expensive equipment requiring specially trained personnel (e.g. in echocardiography). A need therefore exists for a simple method of accurately and sensitively predicting the likelihood of onset of heart failure.

Whilst heart failure can be defined as a symptomatic state i.e. an overt disease or syndrome, patients may frequently pass through a state of asymptomatic cardiac dysfunction i.e. a sub-clinical condition without overt symptoms, before heart failure manifests itself. However, we have now found that not all patients having cardiac dysfunction go on to develop severe heart failure, and that the risk of heart failure for some such people is much greater than for others. To be able to identify those people at particular risk of developing heart failure in order that they may be caught and treated before heart failure occurs would be of great clinical importance; at the moment existing treatments e.g. ACE inhibitors are very expensive and it is not cost-effective for everyone to be treated to try to prevent the onset of heart failure.

We have now found however, that N-terminal pro-Atrial Natriuretic factor (pro-ANF; γ-ANP) levels in patients are a surprisingly accurate predictor of heart failure and cardiovascular mortality. Thus, determination of N-terminal pro-ANF levels in patients may serve to identify those patients at particular risk of developing heart failure.

In particular, our studies have shown that in patients with asymptomatic cardiac dysfunction (e.g. asymptomatic left ventricular dysfunction, as determined by measurement of left ventricular ejection fraction) pro-ANF was the most powerful independent predictor of cardiovascular mortality and the development of severe heart failure.

In one aspect, the present invention thus provides a method of predicting heart failure in a patient, wherein a body fluid of the patient is subjected in vitro to determination of the levels therein of N-terminal pro-ANF or a fragment or polypeptide extension thereof.

Viewed from another aspect, the invention provides a method of screening patients, either for risk of developing heart failure, or lack thereof, wherein a body fluid of the patient is subjected in vitro to determination of the levels therein of N-terminal pro-ANF or a fragment or polypeptide extension thereof and an assessment of the patient's risk is made upon the basis of those levels.

Such screening may be positive i.e. to identify those patients at risk and consequently in need of treatment or negative, i.e. to eliminate those patients who are not at significant risk.

ANF is a potent natriuretic and vasodilatory peptide or mixture of homologous peptides which derive from a common precursor and has been isolated from the atrium of the mammalian heart (DeBold A. J., Borenstein H. B., Veress A. T., Sonnenberg H., Life Sci 1981; 28: 89–94; Flynn T. G., DeBold M. L., DeBold A. J., Biochem Biophys Res Commun 1983; 117: 859–65; Miyata A., Kangawa K., Toshimori T., Hatoh T., Matsuo H., Biochem biophys Res Commun 1985; 129: 248–55; and Thibault G., Garcia R., Gutkowska J., Bilodeau J., Lazure C., Seidah N. G., Chretien M., Genest J., Cantin M., Biochem J. 1987; 21: 265–72). ANF is involved in the hormonal regulation of extracellular fluid volume and blood pressure homeostasis. More recently, ANF has been shown to be secreted from cardiac atria in response to increased atrial pressure and has been implicated in heart failure; ANF levels appear to increase in heart failure, e.g. congestive heart failure (see for example Burnett et al., 1986, Science 231: 1145).

ANF is formed as a high molecular weight precursor, pre-pro ANF and is stored in the atrium as a 126 amino acid peptide prohormone, pro-ANF. The biologically active i.e. mature hormone forms of ANF are formed by proteolytic cleavage upon secretion from cardiocytes, at which time pro-ANF is split into an N-terminal moiety termed N-terminal pro-ANF (ANF(1–98)) and the biologically active hormone (Sundsfjord J. A., Thibault G., Larochelle P., Cantin M., J Clin Endocrinol Metab 1988; 66: 605–10; Thibault G., Murthy K. K., Gutkowska J., Seidah N. G., Lazure C., Chretien M. & Cantin M., Peptides 1988; 9: 47–53; and Itoh H., Nakao K., Sugawara A., Saito Y., Mukoyama M., Morri N., Yamada T., Shiono S., Arai H., Hosoda K., Imura H., J Clin Endocrinol Metab 1988; 67: 429–37).

After its secretion, ANF is rapidly cleared (half-life of 2.5 minutes (Yandle T. G., Richard A. M., Nicholls M. G., Cueno R., Espiner E. A., Livesey J. H., Life Sci 1986: 38; 1827–33)) from plasma by specific binding to abundant peripheral receptors (Maack T., Annu Rev Physiol 1992; 54: 11–27) and, to some extent, also by enzymatic degradation (Stephenson S. L., Kenny A., Biochem J 1987; 243: 183–87). Due to a longer half-life (in rat: 8 times that of ANF (see Thibault et al., 1988 Supra)) the plasma concentration of N-terminal pro-ANF is up to 50 times higher than that of ANF (see Sundsfjord et al., Thibault et al., (1988) and Itoh et al., Supra and Winters C. J., Sallman A. L., Baker B. J., Meadows J., Rico D. M., Vesely D. L., Circulation 1989; 80: 438–49). Correspondingly, plasma N-terminal pro-ANF may better reflect subacute and chronic levels of atrial peptide secretion, but may not be as sensitive as ANF itself to rapid fluctuations in secretion.

The major known stimulus for secretion of the atrial peptides is increased atrial wall stress usually described as increased atrial stretch Dietz J. R., Am J Physiol 1984; 247: R1093–6; and Dietz J. R., Nazian S. J., Vesely D. L., Am J Physiol 1991; 260: H1774–8.

Studies have shown that increased levels of pro-ANF and pro-ANF-derived peptides are secreted in patients with overt heart failure and the determination of pro-ANF or N-terminal pro-ANF levels as well as levels of mature ANF has been proposed as a diagnostic indicator of heart failure (Itoh et al., 1988, Journal of Clinical Endocrinology and Metabolism, 67(3): 429–437). (See also Winters et al., supra and Richards A. M., Cleland J. G. F., Tonolo G., McIntyre G. D., Leckie B. J., Dargie H. J., Ball S. G., Robertson J. I. S., BMJ 1986; 293: 409–12; Mathisen P., Hall C., Simonsen S., Scand J Clin Lab Invest (1993; 53: 41–9; Gottlieb S. S., Kubin M. L., Ahern D., Packer M., J Am Coll Cardiol 1989; 13: 1534–9; Swedberg K., Eneroth P., Kjekshus J., Wilhelmsen L., Circulation 1990; 82: 1730–6; and Svanegaard J., Angelo-Nielsen K., Pindborg T., Br Heart J 1992; 68: 38–42).

As mentioned above, we have now surprisingly shown that N-terminal pro-ANF is an effective predictor of heart failure. In particular, and unpredictably, we have shown that N-terminal pro-ANF is much more effective as a predictor of heart failure than ANF itself.

Preferably, the method of the invention is performed on patients without overt symptoms of heart failure but who are vulnerable to the development of heart failure e.g. patients with asymptomatic cardiac dysfunction who may generally be regarded as at risk of going on to develop overt heart failure. As is well documented in the medical literature, a number of factors may predispose towards heart failure and may be regarded as risk factors for heart failure. These include advanced age, for example over 70 years, hypertension, and any form of heart disease. Thus, patients who have already suffered one or more myocardial infarcts or other manifestation of heart disease, but who do not however exhibit symptoms of heart failure, may be regarded as part of the "at risk" group.

In healthy patients, N-terminal pro-ANF levels in 4the plasma may vary but generally lie below 1400 picomoles/l. Age may influence the normal levels and below about 70 years of age, N-terminal pro-ANF levels are commonly observed below about 1100 picomoles/l. We have found that at just 400 picomoles/l above normal levels, patients are in a high risk group. In such patients it can be predicted that about 50% of the patients will develop heart failure within 3½ years. Thus, generally speaking if plasma levels are higher than 1500 pmols/l e.g. higher than 1600 pmols/l, particularly in patients under 70 years, heart failure can be predicted.

N-terminal pro-ANF levels may be determined using any of the methods and techniques conventional in the art for such determination. Conveniently, such a method may comprise immunoassay e.g. RIA or ELISA. Shinogi & Co. Ltd. in EP-A-0350218 describe a monoclonal antibody recognising the N-terminal of pro-ANF and an immunoassay for pro-ANF using such an antibody. An alternative RIA method is described by Sundsfjord et al. (supra).

The immunoassay determination of N-terminal pro-ANF may be performed using monoclonal or polyclonal antibodies, which may be raised using techniques conventional in the art. For example, antibodies may be made by injecting a host animal, e.g. a mouse or rabbit, with the N-terminal pro-ANF antigen, advantageously a conjugate with an immunogenic protein such as PPD, a protein derivative of tuberculin, Keyhole Limpet Haemocyanin, BSA etc., to provide either a serum containing polyclonal antibodies or spleen cells for fusion to provide hybridomas or immortalised cell lines. Conjugation of hapten to PPD is described by Staros et al., in Analyte Biochem 1986; 156: 220–222. Thus for example we have successfully used a RIA based upon a rabbit polyclonal serum raised against a conjugate of N-terminal pro-ANF coupled to BSA with 1-ethyl-3-(3-dimethyl-aminopropylcarbodiimide).

The immunoassay will conveniently use an antibody in immobilised form, e.g. on microtitre plates, membranes or beads, to isolate the target N-terminal pro-ANF compound. In a sandwich assay, the bound antigen may be labelled using additional soluble antibody, which may be monoclonal or polyclonal and which may either carry a label or, more conveniently, may itself be labelled subsequently by reaction with a secondary antibody carrying a label.

Thus, if the primary antibody according to the invention is raised in mice or rabbits, the labelled secondary antibody may be an antimouse or anti-rabbit antibody.

Suitable labels include radionucleides, fluorescent substances e.g. europium based fluorogens, enzymes, for example as used in ELISA systems employing automated hybrid methods or dyes or coloured particles such as colloidal gold.

Alternatively, a competitive binding assay may be used, wherein a known quantity of labelled N-terminal pro-ANF, or fragment or extension thereof, is added to the analyte solution and contacted with a limited quantity of the immobilised monoclonal antibody, whereby the amount of labelled antigen which is immobilised is inversely proportional to the amount of target antigen present in the analyte.

Conveniently, the components needed to perform the immunoassay will be supplied in kit form. Such a kit would comprise:

(a) an antibody capable of binding to N-terminal pro-ANF and, optionally;

(b) a labelled sample of N-terminal pro-ANF or a fragment or polypeptide extension thereof;

(c) said antibody in non-immobilised form;

(d) a labelled secondary antibody specific to said antibody (c).

In the method of the invention, a quantitative determination of N-terminal pro-ANF levels may be obtained, or a qualitative assessment, indicative of risk of heart failure.

The body fluid on which the determination is performed may be any body fluid in which N-terminal pro-ANF may be located, but conveniently will be plasma or serum. In some cases it may be convenient to extract the peptide, or otherwise treat the sample prior to determination.

Although there appear to be no constraints on the time the method is performed, in patients who have previously suffered a myocardial infarct we have found that a reliable prognosis may be obtained when the N-terminal pro-ANF determination is performed up to 20 days following the infarct e.g. in the period 3–16 days following the infarct.

A further surprising observation is that N-terminal pro-ANF is highly stable on storage. This was not to be predicted as endocrine and neuropeptides of this nature are usually notoriously unstable. Moreover, ANF itself does not show such advantageous stability characteristics. The stability of N-terminal pro-ANF is an important advantage, not only in that it facilitates assay and measurement, but also in that it enables assay to be delayed post-sample collection, for example to enable samples to be mailed or sent to clinical laboratories for analysis i.e. the need to take the sample immediately prior to analysis is avoided. This is a significant advantage for a commercial assay system.

Thus, a further aspect of the invention provides a method of assay of N-terminal pro-ANF in a biological sample, wherein the step of determining the level of N-terminal pro-ANF in the sample is performed not less than 24 hours, e.g. not less than 48 hours after collection of the sample.

Conveniently, the determination will be performed by immunoassay as described above.

N-terminal pro-ANF also has the advantage of long half-life. This makes it particularly advantageous as a parameter of the atrial distension which occurs in cardiac dysfunction; high basal levels of N-terminal pro-ANF permit direct measurement in plasma without chromatography, a greater molar change is observed for a given increase in distension, and plasma levels integrate distension changes overtime.

A major advantage of the method of the invention is that the N-terminal pro-ANF determination can be performed with high specificity and sensitivity leading to an accurate and reliable prediction of heart failure. Prior art methods for detecting cardiac dysfunction and the beginning of heart failure (e.g. echocardiography and catheterisation) do not approach this level of accuracy and sensitivity.

Figure 2:
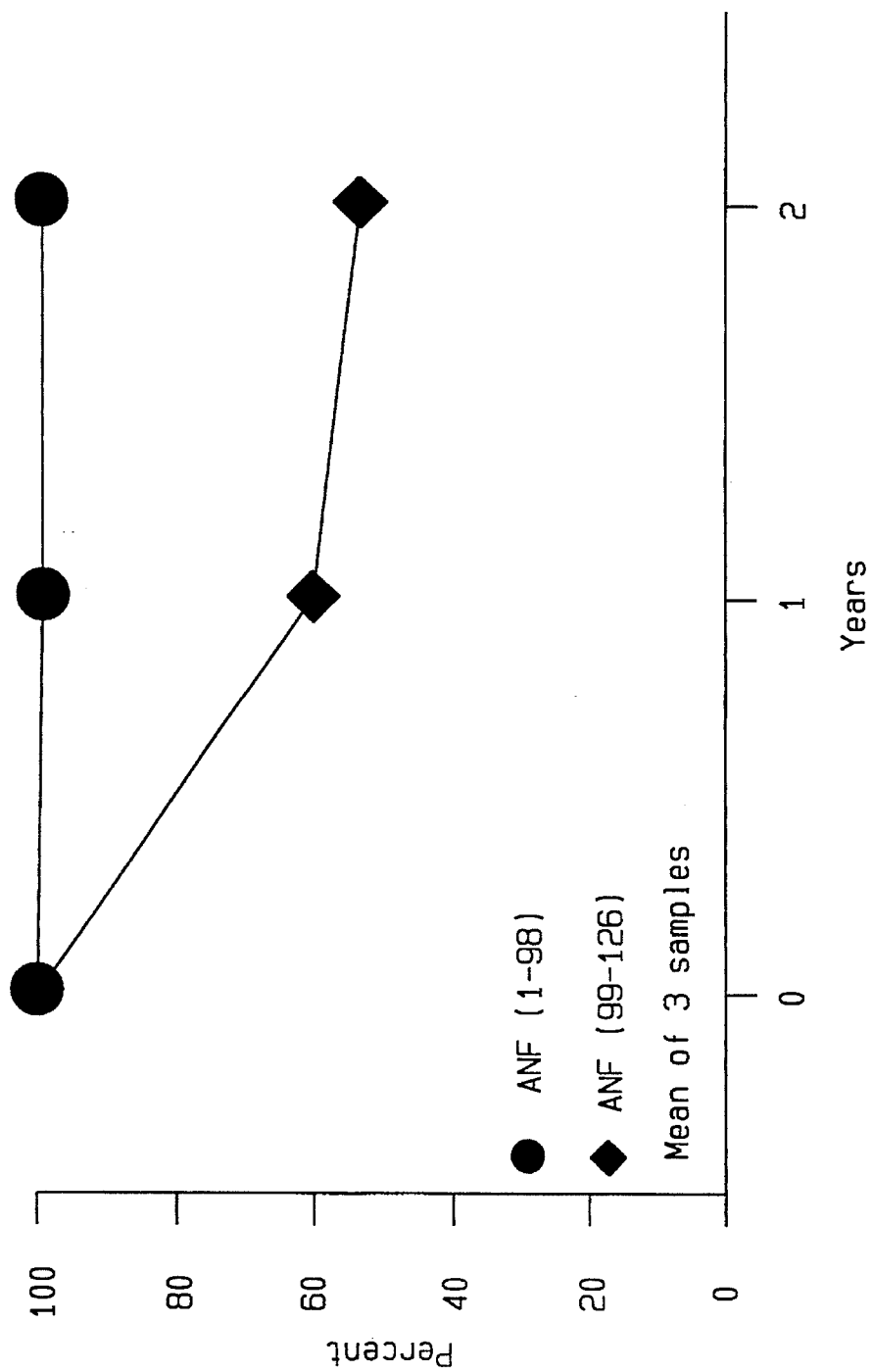

The invention will now be described in greater detail by reference to the following non-limiting Example in which:

FIG. 1 shows life-table curves with respect to total mortality and cardiovascular end points for patient groups divided according to N-terminal pro-ANF quartiles: I: 359 to 769- pmol/l, II: 769 to 1086.25- pmol/, III: 1086.25 to 1666.5- pmol/l, IV: 1666.5 to 5666 pmol/l A Total mortality B Cardiovascular (CV) mortality C Development of severe heart failure D CV mortality of development of severe heart failure; and FIG. 2 shows the stability of pro-ANF in vitro over 48 hours as compared with ANF.

EXAMPLE

The Survival and Ventricular Enlargement (SAVE) study (Pfeffer M. A., Braunwald E., Moye L. A., N Engl J Med 1992; 327: 669–77) provided an excellent opportunity to the prognostic value of atrial peptides measured around the time of hospital discharge in patients at high risk postinfarction, those with left ventricular dysfunction but no overt heart failure. Furthermore, it enabled us to assess whether, because of its stability and longer half-life, N-terminal pro-ANF was superior to ANF itself as a prognostic indicator. In order to determine the independent prognostic value of both ANF and N-terminal pro-ANF, the plasma levels of these substances were measured along with other neurohormones prior to randomization in 246 patients in the SAVE study and correlated by univariate and then by multivariate analyses to subsequent cardiovascular events during an average of 32 months of follow-up.

In order to test whether pro-ANF was of more prognostic value than ANF, plasma concentrations or both were measured in 249 patients in the SAVE study 3–16 days after M1 and related to prognosis. The correlation between ANF and pro-ANF levels was only 0.42, $p<0.001$. A multivariate model which included age, gender, prior M1, hypertension, diabetes, use of thrombolytics and LVEF was constructed to predict subsequent cardiovascular mortality or the development of severe heart failure. When pro-ANF was added to this model, it was found to be the most powerful independent predictor of these events (Wald Chi-Square=22.3, $p<0.001$). When ANF itself was added, it was less useful (Wald Chi-Square= 4.1, $p<0.04$).

The results are shown in FIG. 1. As can be seen from (C), patients in Group IV having pro-ANF levels of 1666 pmoles/l or more, have a 50% greater chance of the development of severe heart failure.

Materials and Methods

The 246 patients included in this study were drawn from the SAVE trial. SAVE is a prospective randomized placebo controlled study that demonstrated that the angiotensin converting enzyme (ACE) inhibitor captopril prolonged survival, decreased the development of severe heart failure and decreased myocardial reinfarction when started 3 to 16 days after myocardial infarction (Pfeffer et al., supra and Moye L. A., Pfeffer M. A., Braunwald E., Am J Cardiol 1991; 68: 70–9D). Only patients with left ventricular dysfunction postinfarction were included in SAVE. Left ventricular dysfunction was defined as LVEF≦40% as measured by equilibrium multigated radionuclide ventriculography. Patients with overt heart failure were excluded. Patients with symptoms or signs of myocardial ischemia not addressed within the 3 to 16 days time window were also excluded. Other exclusion criteria included contraindications to captopril and concurrent medical problems such as renal insufficiency (creatinine>2.5 mg/dl), severe valvular disease, refractory hypertension, malignancy or other conditions thought to limit survival (Moye et al., supra). All patients provided informed consent and in this subgroup agreed to have extra blood samples drawn.

The average age of the patients was 60 (range: 29–79) years and there were 41 females and 205 males. 26.8 percent had a history of hypertension and 18.7% had a history of diabetes. 30.9 percent had a history of prior myocardial infarction. The maximal rise in creatinine kinase during the infarction was 12 times the upper limit of normal. Sixty-one percent of the patients were Killip class 1 and 39% were class 2 or more during the acute infarction. The mean LVEF after the infarction was 31±7%. Thirty-two percent of the patients had received thrombolytics. At the time of neurohumoral blood sampling 32.1% of the patients were receiving diuretics, but no patients were receiving ACE inhibitors. 125 patients were randomized to captopril therapy and 121 were randomized to placebo. The mean period of follow-up was 32 (range 0.03–50.13) months.

Ten Canadian and three American centers participated in this substudy. Blood sampling for measurement of N-terminal pro-ANF was performed between 3 to 16 days (mean 12 days) after infarction just prior to randomization for the main study. The samples were drawn from a venous cannula after the subjects had rested for 30 minutes in the supine position the morning after an overnight fast. After separation of plasma the samples were frozen at −70° C. and sent monthly to the central laboratory (Hopital du Sacre-Coeur de Montreal, Canada) in a frozen condition. After thawing and aspiration of plasma for measurement of other neurohormones (norepinephrine, plasma renin activity, arginine vasopressin and ANF) (Rouleau J. L., Moye L. A., de Champlain J., Klein M., Bichet D., Packer M., Dagenais G., Sussex B., Arnold M., Sestier F., Parker J., McEwan M., Bernstein V., Cuddy T., Delage F., Nadeau C., Lamas G., Gottlieb S., McCans J., Pfeffer M., Am J Cardiol 1991; 68: 80–6D) the samples were refrozen to −70° C. and stored until analysis of N-terminal pro-ANF. Of the 534 SAVE study patients in which neurohormones were measured (Rouleau et al., supra) sufficient plasma for N-terminal pro-ANF measurement was available in 246.

Radioimmunoassay

The analysis of N-terminal pro-ANF was performed by measuring immunoreactive ANF(1–98) (irANF(1–98)) by radioimmunoassay directly in plasma without prior extraction of peptide. The method employed was according to that published by Sundsfjord et al (supra). The detection limit for the assay was: 185 pmol/l. The between assay coefficient of variation was: 7.1% (sample mean: 389 pmol/l, N=10), 5.1% (sample mean: 889 pmol/l, N=10) and 5.2% (sample mean: 1858 pmol/l, N=10). The within assay coefficient of variation was: 5.3% (sample mean: 359 pmol/l, N=10), 2.4% (sample mean: 754 pmol/l, N=10) and 8.5% (sample mean: 8137 pmol/l, N=10).

The other neurohormones reported in this study were measured as earlier described (Mettauer B., Rouleau J. L., Bichet D., Kortas C., Manzini C., Tremblay G., Chatterjee K., Circulation 1986; 73: 409–502; and Wilson N., Ledsome J. R., Keeler R., Rankin A. J., Wade J. P., Cournyea C. A., J immunoassay 1986; 7: 73–96).

Statistical Analysis

The prospectively defined measures of outcome were mortality from all causes, mortality from cardiovascular causes, development of severe heart failure (congestive heart failure requiring ACE inhibition or hospitalization) and the combined end point of cardiovascular mortality or development of severe heart failure. All analyses were performed using significance level of alpha at the 0.05 level, two-sided.

The relationship between each of the specified end points and N-terminal pro-ANF was investigated by both univariate and multivariate analyses using a Cox proportional hazard regression model. The assumption of a constant hazard ratio over time for the Cox regression model was tested and verified. Kaplan-Meier estimates for the distribution of time from randomization to individual end points were used to evaluate the importance of differences among the life table curves. The equality among these life table curves were analyzed by a log-rank test.

The relative risks (RR) for each individual end point were calculated for an increment of 1.96 standard deviation of normal controls of N-terminal pro-ANF and other neurohormones. One hundred and thirty-four age-matched healthy individuals (60±16 years of age) from Oslo, Norway were used as normal controls for N-terminal pro-ANF. The normal control group for the other neurohormones was thirty-eight age-matched (57±7 years of age) healthy volunteers working in the various participating centers.

Results

Compared to age-matched controls mean N-terminal pro-ANF and ANF values were elevated in SAVE patients (N-terminal pro-ANF: 1331.5±820.1 vs 587.5±230.9 pmol/l, $p<0.001$; ANF: 78.4±84.5 vs 21.1±9.5 pg/ml $p<0.001$). Other neurohormones such as norepinephrine (30.58±191.8 vs 221.5±86.9 pg/ml for controls, $p<0.001$), plasma renin activity (2.9±4.0 vs 1.2±1.2 ng/ml/h for controls, $p<0.001$) and arginine vasopressin (2.2±9.5 vs 0.7±0.3 pg/ml for controls, $p=0.01$), were also increased. The correlation between N-terminal pro-ANF and the other neurohormones was generally poor. The best correlation was found between N-terminal pro-ANF and ANF itself ($r=0.42$, $p<0.001$). Only a weak correlation was found between N-terminal pro-ANF and norepinephrine ($r=0.21$, $p<0.001$) and plasma renin activity ($r=0.17$, $p=0.007$). There was no significant correlation between N-terminal pro-ANF and arginine vasopressin.

Relationship with Subsequent Mortality and Morbidity

Forty-seven patients died during the follow-up period. Thirty-eight patients died of cardiovascular causes and 25 of these in the first year. Forty-three patients developed severe heart failure (requiring open-labelled ACE inhibition or hospitalization for heart failure) and 64 reached the combined end point of either death of cardiovascular causes or development of severe heart failure.

By univariate analysis there was a strong relationship between N-terminal pro-ANF and these end points (Death: Wald $X^2=24.92$, RR (with 95% CI)=1.30 (1.17–1.44), $p<0.001$; cardiovascular death: Wald $X^2=28.11$, RR+1.34 (1.20–1.49), $p<0.001$; 1-year cardiovascular death: Wald $X^2=18.21$, RR=1.31 (1.16–1.48), $p<0.001$; severe heart failure: Wald $X^2=59.17$, RR=1.49 (1.35–1.66), $p<0.001$; cardiovascular death or severe heart failure: Wald $X^2$— 56.62, RR=1.40 (1.28–1.53), $p<0.001$. This is well illustrated in FIG. 1 where life-table curves for 4 of these end points are constructed after separating patients into N-terminal pro-ANF quartiles.

N-terminal pro-ANF and ANF levels were higher in all groups of patients with an event (table 1). In order to compare the predictive power of N-terminal pro-ANF to that of ANF, a Cox proportional hazard model was constructed which included both N-terminal pro-ANF and ANF levels (table 1). Controlling for the level of ANF it was found that N-terminal pro-ANF was significantly related to each of the end points. On the other hand, after controlling for the effect of N-terminal pro-ANF, the ANF level was not related to any of the five end points. Evidently, among the two neurohormones N-terminal pro-ANF was the stronger predictor of all the five end points studied.

When N-terminal pro-ANF was added to a multivariate model of clinical and laboratory variables known to influence survival (table 2), it was found to be a powerful independent predictor of long-term outcome. By multivariate analyses, N-terminal pro-ANF was independently related to death, cardiovascular death, 1-year cardiovascular death, severe heart failure, and cardiovascular death or severe heart failure (table 2). For the combined end point of cardiovascular death or severe heart failure N-terminal pro-ANF was the best clinical or laboratory predictor, even superior to age, LVEF and prior myocardial infarction.

To compare the predictive power of N-terminal pro-ANF to that of the other neurohormones in multivariate analysis these variables were also included in the model (table 3). The superior prognostic value of N-terminal pro-ANF over these other neurohormones (ANF, norepinephrine, plasma renin activity and arginine vasopressin) was evident in that while N-terminal pro-ANF retained its significant relation to all the end points, only norepinephrine showed a significant relation and only to the end points severe heart failure and the combination cardiovascular death or severe heart failure. With respect to these end points however, norepinephrine was a considerably weaker predictor than N-terminal pro-ANF as evidenced from the Wald $X^2$ values.

TABLE 1

COMPARING THE PREDICITVE POWER OF N-TERMINAL PROANF AND ANF

| | N-terminal proANF | | | | |
|---|---|---|---|---|---|
| | No | Yes | | | |
| | Mean ± Std | | Wald | | Relative Risk |
| Event | (n) | | Chi-square | P-value | (95% CI) |
| Death | 1211 ± 641 (199) | 1841 ± 1220 (47) | 25.35 | <0.001 | 1.39 (1.22–1.58) |
| Cardiovascular Death | 1215 ± 705 (208) | 1967 ± 1086 (38) | 25.77 | <0.001 | 1.40 (1.23–1.60) |
| 1-year cardiovascular death | 1252 ± 743 (221) | 2035 ± 1110 (25) | 14.51 | <0.001 | 1.35 (1.16–1.58) |
| Development of Heart Failure | 1170 ± 603 (203) | 2094 ± 1206 (43) | 49.72 | <0.001 | 1.50 (1.34–1.67) |
| Cardiovascular death or development of heart failure | 1127 ± 560 (182) | 1912 ± 1119 (64) | 48.58 | <0.001 | 1.42 (1.29–1.57) |

| | ANF | | | | |
|---|---|---|---|---|---|
| | No | Yes | | | |
| | Mean ± Std | | Wald | | Relative Risk |
| Event | (n) | | Chi-square | P-value | (95% CI) |
| Death | 77 ± 89 (199) | 84 ± 65 (47) | 2.80 | 0.094 | 0.91 (0.83–1.02) |
| Cardiovascular Death | 76 ± 88 (108) | 93 ± 65 (38) | 1.61 | 0.204 | 0.94 (0.85–1.04) |
| 1-year cardiovascular death | 77 ± 87 (221) | 93 ± 62 (25) | 0.48 | 0.489 | 0.96 (0.8–1.08) |
| Development of Heart Failure | 72 ± 87 (203) | 108 ± 65 (43) | <0.01 | 0.968 | 0.99 (0.9–1.07) |
| Cardiovascular death or development of heart failure | 72 ± 90 (182) | 96 ± 63 (64) | 0.37 | 0.544 | 0.98 (0.92–1.04) |

P-values calculated by Cox proportional hazard analysis. For each end point, the only independent variables in the models were N-terminal proANF and ANF.
Relative risk calculated for an increment of 1.96 standard deviation of normal controls (452.52 pmol/l of N-terminal proANF; 18.56 pg/ml of ANF).

TABLE 2

RELATIONS BETWEEN END POINTS AND N-TERMINAL PROANF IN MULTIVARIATE ANALYSIS

| | Event | | | | | | | | |
|---|---|---|---|---|---|---|---|---|---|
| | Death | | | Cardiovascular death | | | 1-year cardiovascular death | | |
| Variable | P-Value | Wald $\chi^4$ | Relative Risk (95% CI) | P-Value | Wald $\chi^4$ | Relative Risk (95% CI) | P-Value | Wald $\chi^4$ | Relative Risk (95% CI) |
| Age | 0.236 | 1.40 | 1.11 (0.93–1.32) | 0.376 | 0.79 | 1.09 (0.90–1.34) | 0.999 | <0.01 | 1.00 (0.79–1.26) |
| Gender male | 0.378 | 1.17 | 0.67 (0.33–1.38) | 0.138 | 2.20 | 0.56 (0.26–1.21) | 0.003 | 8.99 | 0.27 (0.11–0.63) |
| Prior MI | 0.194 | 1.69 | 1.51 (0.81–2.79) | 0.236 | 1.40 | 1.52 (0.76–3.02) | 0.069 | <0.01 | 1.01 (0.42–2.39) |
| Diabetes | 0.287 | 1.13 | 1.42 (0.74–2.73) | 0.645 | 0.21 | 1.19 (0.57–2.46) | 0.768 | 0.09 | 0.87 (0.34–2.24) |
| Hypertension | 0.751 | 0.10 | 0.90 (0.46–1.76) | 0.710 | 0.14 | 0.97 (0.41–1.85) | 0.639 | 0.19 | 0.81 (0.31–2.11) |
| LVEF | <0.001 | 11.13 | 0.70 (0.56–0.86) | <0.001 | 16.41 | 0.61 (0.48–0.78) | <0.001 | 15.56 | 0.55 (0.41–0.74) |
| Thrombolysis | 0.753 | 0.10 | 0.88 (0.41–1.92) | 0.491 | 0.47 | 0.72 (0.29–1.83) | 0.575 | 0.31 | 0.74 (0.26–2.12) |
| N-terminal proANF | 0.033 | 4.57 | 1.17 (1.01–1.36) | 0.015 | 5.89 | 1.21 (1.04–1.42) | 0.014 | 6.03 | 1.27 (1.05–1.54) |

| | Event | | | | | |
|---|---|---|---|---|---|---|
| | Development of Heart Failure | | | Cardiovascular Death or Development of Heart Failure | | |
| Variable | P-Value | Wald $\chi^4$ | Relative Risk (95% CI) | P-Value | Wald $\chi^4$ | Relative Risk (95% CI) |
| Age | 0.014 | 6.11 | 0.80 (0.67–0.95) | 0.097 | 2.76 | 0.89 (0.77–1.02) |
| Gender male | 0.127 | 2.33 | 0.56 (0.26–1.18) | 0.030 | 4.73 | 0.52 (0.28–0.94) |
| Prior MI | 0.043 | 4.09 | 2.11 (1.02–4.35) | 0.211 | 1.56 | 1.44 (0.81–2.54) |
| Diabetes | 0.198 | 1.66 | 1.60 (0.78–3.27) | 0.262 | 1.26 | 1.29 (0.78–1.48) |
| Hypertension | 0.151 | 2.06 | 1.65 (0.83–3.27) | 0.330 | 0.95 | 1.32 (0.76–2.30) |
| LVEF | 0.406 | 0.69 | 0.90 (0.71–1.15) | 0.006 | 7.46 | 0.77 (0.64–0.93) |
| Thrombolysis | 0.096 | 0.02 | 1.05 (0.48–2.29) | 0.576 | 0.31 | 0.53 (2.43–1.59) |
| N-terminal proANF | <0.001 | 31.73 | 1.49 (1.30–1.71) | <0.001 | 17.01 | 1.37 (1.22–1.55) |

P-values calculated by Cox proportional hazard anaylsis.
Relative risk calculated for an increment of 5 years of age, 5% units of LVEF and 1.96 standard deviation of normal controls of N-terminal proANF (452.52 pmol/l).

TABLE 3

COMPARING THE PREDICTIVE POWER OF NEUROHORMONES IN MULTIVARIATE ANALYSIS

| | Event | | | | | | | | |
|---|---|---|---|---|---|---|---|---|---|
| | Death | | | Cardiovascular death | | | 1-year cardiovascular death | | |
| Variable | P-Value | Wald $\chi^4$ | Relative Risk (95% CI) | P-Value | Wald $\chi^4$ | Relative Risk (95% CI) | P-Value | Wald $\chi^4$ | Relative Risk (95% CI) |
| N-terminal ProANF | 0.004 | 8.45 | 1.30 (1.09–1.55) | 0.002 | 9.24 | 1.34 (1.11–1.62) | 0.002 | 9.41 | 1.48 (1.15–1.89) |
| ANF | 0.053 | 3.75 | 0.90 (0.83–1.00) | 0.082 | 3.03 | 0.91 (0.81–1.01) | 0.214 | 1.54 | 0.91 (0.78–1.06) |
| Norepinephrine | 0.915 | 0.01 | 1.01 (0.79–1.31) | 0.805 | 0.06 | 0.96 (0.72–1.29) | 0.679 | 0.17 | 0.91 (0.59–1.41) |
| Plasma renin | 0.963 | <0.01 | 1.00 | 0.912 | 0.01 | 1.01 | 0.247 | 1.34 | 0.85 |

TABLE 3-continued

COMPARING THE PREDICTIVE POWER OF NEUROHORMONES
IN MULTIVARIATE ANALYSIS

| activity | | | | | | | | | |
|---|---|---|---|---|---|---|---|---|---|
| | | | (0.89–1.13) | | | (0.88–1.15) | | | (0.64–1.12) |
| Arginine vasopressin | 0.724 | 0.12 | 1.00 | 0.744 | 0.11 | 1.00 | 0.480 | 0.50 | 1.01 |
| | | | (0.96–1.03) | | | (0.98–1.03) | | | (0.96–1.03) |

| | Event | | | | | |
|---|---|---|---|---|---|---|
| | | Development of Heart Failure | | | Cardiovascular Death or Development of Heart Failure | |
| Variable | P-Value | Wald $\chi^4$ | Relative Risk (95% CI) | P-Value | Wald $\chi^4$ | Relative Risk (95% CI) |
| N-terminal ProANF | <0.001 | 26.26 | 1.50 (1.26–1.74) | <0.001 | 24.31 | 1.40 (1.23–1.60) |
| ANF | 0.918 | 0.01 | 1.00 (0.93–1.07) | 0.378 | 0.78 | 0.97 (0.91–1.04) |
| Norepinephrine | 0.012 | 5.26 | 1.31 (1.04–1.66) | 0.003 | 4.53 | 1.24 (1.02–1.51) |
| Plasma renin activity | 0.325 | 0.97 | 1.05 (0.95–1.16) | 0.676 | 0.17 | 1.02 (0.93–1.12) |
| Arginine vasopressin | 0.784 | 0.08 | 0.99 (0.92–1.07) | 0.943 | <0.01 | 1.00 (0.98–1.02) |

P-values calculated by Cox proportional hazard anaylsis.
Relative risk calculated for an increment of 1.96 standard deviation of normal controls for each neurohormone (452.52 pmol/l of N-terminal proANF, 18.56 pg/ml of ANF, 170.36 pg/ml of noreinephrine, 2.29 ng/ml/h of plasma renin activity and 0.61 pg/ml of arginine vasopressin).

DISCUSSION

This study indicates that N-terminal pro-ANF measured around the time of hospital discharge is the best neurohumoral predictor of subsequent cardiovascular events in patients with left ventricular dysfunction postinfarction. This was particularly true for the development of severe heart failure and the combined end point of severe heart failure and cardiovascular death. For these end points N-terminal pro-ANF was not only the most powerful neurohormonal predictor, it was also by far the best predictor of all clinical or laboratory variables included in the analysis.

This is the first large scale study evaluating the long-term prognostic value of neurohumoral activation measured around the time of hospital discharge postinfarction in patients at high risk, those with left ventricular dysfunction. As was found in chronic heart failure (Gottlieb et al., and Swedberg et al., supra and Cohn J. N., Levine T. B., Olivari M. T., Garberg V., Lura D., Francis G., Simon A., Rector T., N Engl J Med 1984; 311: 819–23) in this study, all neurohormones correlated with subsequent mortality in univariate analysis (data not shown). However, as in chronic heart failure, when other important clinical and laboratory variables were considered along with neurohormones in a multivariate analysis, the correlation between neurohormones and subsequent mortality was much weaker and in most cases not significant. This was true for all neurohormones except for N-terminal pro-ANF which continued to be strongly correlated with both survival and the development of severe heart failure, in the latter case being even more so than age, LVEF or previous myocardial infarction. For a 60 year old male postinfarction patient without diabetes, hypertension, a previous myocardial infarction or thrombolytic therapy, but with an LVEF of 30%, an increase in plasma N-terminal pro-ANF of 452.5 pmol/l (1.96 SD of normal controls) above the mean of 1331.5 pmol/l implied a 21% rise in risk of cardiovascular death and a 49% rise in the risk of developing severe heart failure.

Why N-terminal pro-ANF should be superior to other neurohormones in predicting subsequent cardiovascular mortality and morbidity is uncertain. However, considering the close correlation between atrial peptide plasma levels and atrial pressure (Richards et al., and Mathisen et al., supra), this result points to increased atrial pressure or possibly atrial wall stress (Edwards B. S., Zimmerman R. S., Schwab T. R., Heublein D. M., Burnett J. C., Circ Res 1988; 62: 191–5; and Hintze T. H., McIntyre J. J., Patel M. B., Shapiro J. T., DeLeonardis M., Seballos G. A., Loug A. V., Am J Physiol 1989; 256: H713–H719) at the time of hospital discharge postinfarction as an ominous prognostic sign, even when symptoms of heart failure are not present. At least two interrelated explanations of this relationship between atrial pressure and prognosis are possible. First, as atrial pressures are the result of the convergence of both systolic and diastolic function, and the prognostic value of N-terminal pro-ANF is independent of LVEF, it is possible that diastolic dysfunction itself postinfarction is a poor prognostic sign. Or, alternatively, as increasing filling pressures are a major stimulus for eccentric ventricular hypertrophy (Grossman W., Jones D., McLaurin L. P., J Clin Invest 1975: 56; 56–64), increased atrial pressures may be a marker of patients at risk of ventricular dilatation postinfarction. Ventricular dilatation postinfarction is known to be a major if not the major independent predictor of mortality postinfarction (White H. D., Norris R. M., Brown M. R., Brandt P. W. T., Whitlock R. M. L., Wild C. J., Circulation 1987; 76(1): 44).

N-terminal pro-ANF fared considerably better than ANF as a prognostic indicator. This was an unexpected finding considering the assumed equimolar secretion of the two peptides. The difference may be explained by the longer half-life of N-terminal pro-ANF, making it a better integrator over time of atrial peptide secretion. Another important and probably highly relevant difference between the peptides is the in vitro stability. While ANF is known to be subject to in vitro degradation possibly even under −80° C. of storage (Nelesen R. A., Dimsdale J. E., Ziegler M. G., Circulation 1992; 86: 463), experiments in our laboratory indicate that N-terminal pro-ANF immunoreactivity is well preserved after storage for up to 3 days at room temperature and 2 years at −80° C. (unpublished data). The peptide has also been found resistant to at least two repeated freezing and thawing cycles.

Information pertaining to the prognosis of patients after myocardial infarction is important in the selection of patients for different treatment regimens. LVEF is known to be a strong predictor of long term outcome postinfarction (White et al., supra) and has been used to identify high risk patients, those most likely to benefit from interventions designed to prolong survival (Pfeffer et al., supra; N Engl J Med 1991; 325: 293–302. Cohn J. N., Johnson G., Ziesche S., Cobb F., France G., Tristani F., Smith R., Dunkman W., Loeb H., Wong M., Bhat G., Goldman S., Fletcher R., Doherty J., Hughes C., Carson P., Cintron G., Shabetai R., Haakenson C., N Engl J Med 1991; 325: 303–10). According to the present findings, measurement of plasma N-terminal pro-ANF provides information on long term outcome that is additive and independent of LVEF. Whether the N-terminal pro-ANF plasma levels can be of general use as an additional parameter in making treatment decisions is a question that might be addressed in future studies. However, judging from this study, it would appear to be useful in this high risk subgroup of patients. This subject is of special interest in circumstances where other parameters of left ventricular function are not readily available. In such a setting N-terminal pro-ANF may represent a new and important tool for the practicing physician.

SUMMARY

Because of a longer half-life and stability the N-terminal of ANF prohormone (N-terminal pro-ANF) may be a better integrator of atrial peptide secretion than ANF itself. The prognostic value of N-terminal pro-ANF plasma levels measured after myocardial infarction was tested in 246 patients from the SAVE study. N-terminal pro-ANF was a much stronger predictor of survival than ANF itself. Furthermore, in multivariate analysis of cardiovascular mortality and development of heart failure N-terminal pro-ANF in contrast to ANF and other neurohormones was still a powerful and independent predictor. The measurement of N-terminal pro-ANF supplements currently applied clinical and objective assessments and provides an important independent predictor of prognosis with respect to cardiovascular mortality and development of heart failure.

I claim:

1. A method of testing for heart failure risk in an asymptomatic patient, which comprises contacting a body fluid sample from the asymptomatic patient with an antibody which specifically binds to N-terminal Pro-ANF and detecting the formation of an immune complex by immunoassay, and comparing the peptide level thus obtained to control levels as an indication of said risk.

2. A method of screening asymptomatic patients, either for risk of developing heart failure, or lack thereof, which comprises contacting a body fluid sample from the asymptomatic patient with an antibody which specifically binds to N-terminal Pro-ANF and detecting the formation of an immune complex by immunoassay, and assessing the patient's risk of developing heart failure upon the basis of said levels.

3. A method as claimed in claim 1 or claim 2 wherein said human is selected from humans over 70 years of age, humans exhibiting hypertension and humans having or having previously had a form of heart disease.

4. A method as claimed in claim 1 or 2 wherein said body fluid comprises plasma.

5. A method as claimed in claim 4 wherein a plasma level of higher than 1500 pmols N-terminal pro-ANF/L plasma is taken as indicative of risk of development of heart failure.

6. A method as claimed in claim 1 or claim 2 wherein said body fluid comprises plasma.

7. A method as claimed in claim 6 wherein a plasma level of higher than 1500 pmols N-terminal pro-ANF/l plasma is taken as indicative of risk of development of heart failure.

8. A method as claimed in claim 1 or claim 2, wherein the level of N-terminal pro-ANF is determined.

9. A method as claimed in claim 1 or claim 2, wherein an immunoassay is performed using an antibody raised against N-terminal pro-ANF.

10. The method of claim 1 wherein said contacting step is conducted using components from a kit comprising
   (a) an antibody which specifically binds to N-terminal pro-ANF, and at least one of the following;
   (b) a labeled sample of N-terminal pro-ANF;
   (c) an antibody, as defined in (a), in non-immobilized form; or
   (d) a labeled secondary antibody specific to said antibody (c).

11. The method of claim 2 wherein said contacting step is conducted using components from a kit comprising
   (a) an antibody which specifically binds to N-terminal pro-ANF, and at least one of the following;
   (b) a labeled sample of N-terminal pro-ANF;
   (c) an antibody, as defined in (a), in non-immobilized form; or
   (d) a labeled secondary antibody specific to said antibody (c).

* * * * *